United States Patent
Khosravi et al.

(12) 
(10) Patent No.: US 6,231,562 B1
(45) Date of Patent: *May 15, 2001

(54) METHODS AND APPARATUS FOR TREATING ANEURYSMS AND ARTERIO-VENOUS FISTULAS

(75) Inventors: Farhad Khosravi, San Mateo; Amir Abolfathi; Michael Hogendijk, both of Palo Alto, all of CA (US)

(73) Assignee: Endotex Interventional Systems, Inc., Cupertino, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/095,668

(22) Filed: Jun. 10, 1998

Related U.S. Application Data

(63) Continuation of application No. 08/504,293, filed on Jul. 19, 1995, now Pat. No. 5,785,679.

(51) Int. Cl.[7] ................................................... A61M 31/00
(52) U.S. Cl. ............... 604/507; 604/103.02; 604/103.07; 606/194
(58) Field of Search ................................... 604/104, 158, 604/173, 264, 272, 48, 500, 506, 507, 508, 509, 523, 96.01, 99.01, 101.01, 101.05, 102.01, 103.02, 103.06, 103.07, 164.01; 606/191–198; 623/1, 11, 12, 66; 128/898

(56) References Cited

U.S. PATENT DOCUMENTS

| | | | |
|---|---|---|---|
| 4,708,718 | * | 11/1987 | Daniels ................................... 604/20 |
| 4,731,055 | * | 3/1988 | Melinyshyn et al. . |
| 5,100,429 | * | 3/1992 | Sinofsky et al. .......................... 623/1 |
| 5,213,580 | * | 5/1993 | Slepian et al. ............................ 623/1 |
| 5,328,471 | * | 7/1994 | Slepian ................................. 604/101 |
| 5,342,301 | * | 8/1994 | Saab ..................................... 604/101 |
| 5,443,495 | * | 8/1995 | Buscemi et al. ...................... 606/191 |
| 5,456,712 | * | 10/1995 | Maginot ................................... 623/1 |
| 5,522,880 | * | 6/1996 | Barone et al. ........................ 606/195 |
| 5,769,870 | * | 6/1998 | Salahich et al. . |

\* cited by examiner

Primary Examiner—Anhtuan T. Nguyen
Assistant Examiner—Jeremy Thissell
(74) Attorney, Agent, or Firm—Lyon & Lyon LLP

(57) ABSTRACT

Methods and apparatus are provided for temporarily excluding an aneurysm or an arterio-venous fistula from a flow path by transluminally disposing a hollow balloon catheter structure within the aneurysm so that its proximal and distal ends extend past the aneurysm while maintaining continuity of the flow path, and then injecting a synthetic molding material or a biological hardening agent into the aneurysm cavity to cause solidification of the volume within the cavity. Once the material within the excluded aneurysm has solidified, the balloon catheter structure is deflated and removed, so that the hardened mass forms a new lining for the organ or vessel, and relieves the weakened tissue of the aneurysm or fistula from further flow-induced stress.

27 Claims, 7 Drawing Sheets

METHODS AND APPARATUS FOR TREATING ANEURYSMS AND ARTERIO-VENOUS FISTULAS

This application is a continuation of application Ser. No. 08/504,293, filed Jul. 19, 1995, now U.S. Pat. No. 5,785,679.

FIELD OF THE INVENTION

The present invention relates generally to minimally-invasive techniques for repairing aneurysms occurring in hollow-body biological organs and vessels, for example, the aorta and iliac arteries, and arterio-venous fistulas. More particularly, the present invention relates to methods and apparatus for repairing aneurysms and fistulas using hardening agents that exclude the weakened tissue from a flow path.

BACKGROUND OF THE INVENTION

In recent years a number of minimally-invasive techniques have been developed to repair aneurysms occurring in hollow-body biological organs and vessels, for example, the aorta, using stent-graft techniques. These techniques generally seek to "re-line" the blood flow path through the organ, for example, by fixing a fabric material across the section of weakened tissue. The fabric is then held in place with one or more stents, which may be implanted, for example, using a balloon catheter. Such arrangements are described, for example, in Parodi U.S. Pat. 5,219,355 and European Application No. 0 461 791.

Such methods and apparatus are suitable for use in only a limited number of aneurysm situations, however. In particular, for such previously known methods to be effective, the portions of the organ proximal and distal to the aneurysm (i.e., the proximal neck and the distal cuff of the aneurysm) must be relatively straight to permit the stents and liner to obtain sufficient apposition on the organ or vessel walls.

Moreover, for such previously known methods to be effective, it is important that the nondilated diameter of the aorta proximal to the aneurysm be the same (within a few millimeters) of the nondilated portion of the distal cuff. Otherwise, the stent or stents selected to fasten the ends of the liner to the proximal and distal regions of the nondilated aorta may be incapable of the range of diametral expansion needed to engage both the proximal and distal regions.

If either of the above-described conditions occur, i.e., either insufficient lengths of the proximal neck and/or distal cuff, or large diametral discrepancies between those regions, there may be leakage at either or both of the proximal and distal ends of the graft. Consequently, the aneurysm may remain subjected to flow-induced pressure, with concomitant risk of rupture. These drawbacks of previously known minimally-invasive stent graft techniques are described by T. Chuter et al. in *Endoluminal Vascular Prostheses*, Little Brown & Co. (1995), Chapter 2 at pp. 23–33, which is incorporated herein by reference.

As further described in the foregoing text, while complicated bifurcated endovascular grafts may be used in those cases where the distal cuff is insufficiently long, use of such previously known grafts is limited to those situations where there is no aneurysm of the iliac arteries. See, for example, Chapter 4 of the foregoing text, which is incorporated herein by reference, especially at pp. 57–59 discussing patient selection criteria. Moreover, the use of bifurcated grafts, while increasing the number of candidates for minimally-invasive procedures, raises additional issues of graft sizing.

In addition to the restriction of previously known methods and apparatus mostly to those cases where some nondilated length of the aorta and/or distal cuff remains, the occurrence of aneurysms in organs and vessels other than the aorta, for example, in the iliac arteries, is untreatable using previously known minimally-invasive techniques.

While certain techniques have been recently developed for defining a cavity within an aneurysm and then filling the cavity with a heat activated molding material, as described, for example, in International Application PCT/U.S. Ser. No. 94/09837, these techniques do not provide for continuity of the flow path during the treatment period. Techniques such as described in the foregoing International Application therefore do not appear suitable for use in vascular aneurysms or in other applications where the flow path must remain uninterrupted.

In view of the foregoing, it would be desirable to provide minimally-invasive methods and apparatus suitable for repairing aneurysms that can be used in patients having relatively short lengths of nondilated aorta above the aneurysm, with little or no distal cuff length.

It further would be desirable to provide minimally-invasive methods and apparatus suitable for repairing aneurysms having large changes in diameter in the nondilated aorta regions proximal and distal to the aneurysm.

It also would be desirable to provide minimally-invasive methods and apparatus suitable for repairing aneurysms in hollow-body organs and vessels other than the aorta, for example, in the iliac arteries, and for repairing arterio-venous fistulas.

It would be yet further desirable to provide minimally-invasive methods and apparatus suitable for treating aneurysms in hollow-body organs and vessels so as to exclude the aneurysm entirely from either the hemodynamic circuit in the vascular system or other biological fluids or materials flowing through hollow-body organs of a nonvascular nature, so as to prevent leakage flow to the weakened aneurysm tissue, and thereby reduce the risk of rupture.

SUMMARY OF THE INVENTION

In view of the foregoing, it is an object of this invention to provide minimally-invasive methods and apparatus suitable for repairing aneurysms in hollow-body organs and vessels defining a flow path that can be used in patients having relatively short lengths of nondilated organ above the aneurysm neck, and little or no distal cuff length, while retaining continuity of the flow path.

It is a further object of the present invention to provide minimally-invasive methods and apparatus suitable for repairing aneurysms in hollow-body organs and vessels having large changes in diameter in the nondilated organ or vessel regions proximal and distal to the aneurysm.

It is another object of this invention to provide minimally-invasive methods and apparatus suitable for repairing aneurysms in hollow-body organs and vessels other than the aorta, for example, in the iliac arteries, and for repairing arterio-venous fistulas. The methods and apparatus of the present invention also find applicability in gastro-intestinal, respiratory, reproductive organ, urethral applications and elsewhere where it is desirable to "reline" a hollow-body organ and vessels.

It is yet another object of this invention to provide minimally-invasive methods and apparatus suitable for treating aneurysms in hollow-body organs and vessels so as to exclude the aneurysm entirely from, for example, the hemodynamic circuit, so as to prevent leakage flow to the weakened aneurysm tissue, and thereby reduce the risk of rupture.

These and other objects of the invention are accomplished in accordance with the principles of the invention by providing methods and apparatus for temporarily excluding an aneurysm from a flow path, for example, the blood flow path in the vascular system, while maintaining continuity of the flow path. A substance, such as a molding material or a hardening agent, is then injected into the aneurysm cavity. The injected substance causes, for example, thrombosis of the blood located within the cavity, or solidifies in response to exposure to an aqueous solution (e.g., blood) present in the cavity or in response to the application of heat.

In accordance with the invention, a hollow balloon catheter structure or other means of temporarily excluding flow from the aneurysm cavity, while providing uninterrupted flow through a main lumen, is endoluminally disposed within the aneurysm so that its proximal and distal ends extend past the aneurysm. The balloon catheter structure is dimensioned to isolate the aneurysm cavity from the blood flow path, while permitting blood flow to pass through a lumen in the structure uninterrupted. A suitable molding material, for example, a hydrogel or polymer of a resorbable or permanent nature, a blood hardening agent, for example, fibrin or a tissue material, for example, collagen, is then injected into the aneurysm cavity, either by a catheter, laparoscopically, or by invasive surgical means.

Once the molding material has hardened, for example, either by inducing thrombosis of blood captured within the cavity or by body-temperature activation of the injected substance itself or other means for activation of the injected substance, the balloon catheter structure is deflated and removed. The hardened mass of thrombus or polymer thus forms the new lining of the organ, and relieves the weakened tissue of the aneurysm from further fluid flow stress.

In accordance with alternative embodiments of the present invention, aneurysms in the iliac arteries may also be treated using a combination of hollow balloon catheter and conventional catheter which are abutted against one another to form a mold for the new inner lining of the organ. That new inner liner is again formed by introducing a molding material or hardening agent into the cavity, defined by the walls of the aneurysm, the hollow balloon catheter and the conventional balloon catheter, to produce a coherent thrombosis or molded mass.

In yet further alternative embodiments, a wire mesh member may be disposed on the exterior surface of the hollow balloon catheter structure to serve as a framework for retaining the coherency of the thrombus formed by introduction of the hardening agent or molding material.

Further features of the invention, its nature and various advantages will be more apparent from the accompanying drawings and the following detailed description of the preferred embodiments.

DETAILED DESCRIPTION OF THE PREFERRED EMBODIMENTS

The present invention provides entirely new methods and apparatus for treatment of aneurysms occurring in hollow-body organs or vessels that overcome the limitations of previously known minimally-invasive methods. In particular, the methods and apparatus of the present invention permit an aneurysm to be isolated from flow-induced stress or other pressure by forming a solid mass of thrombus or molding material that serves as a new lining for the organ or vessel, while relieving flow-induced stresses in the weakened tissue of the aneurysm. During treatment, flow path across the aneurysm remains uninterrupted.

Figure 1:
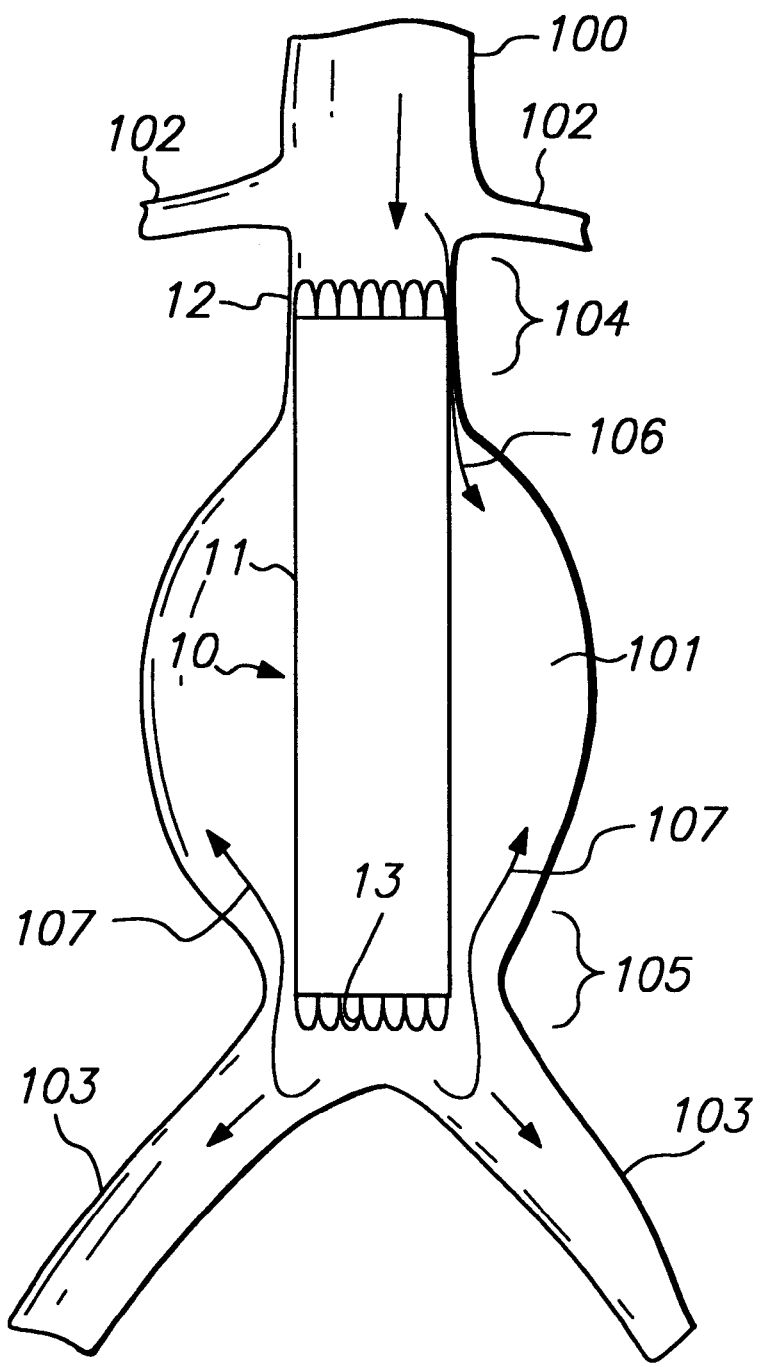
FIG. 1 is an elevation view, partly in section, of an abdominal aorta having implanted within it a previously known stent graft.

Referring to FIG. 1, a previously known stent graft arrangement, such as described in Parodi U.S. Pat. No. 5,219,355 and European Application No. 0 461 791, is described. As illustratively shown in FIG. 1, stent graft 10 is disposed across the region of the aneurysm 101 in aorta 100, which is located between renal arteries 102 and iliac arteries 103. Aneurysm 101 includes a proximal nondilated region of aorta 100 above the aneurysm referred to as "proximal neck" 104, and a distal region just above the bifurcation for iliac arteries 103 referred to as "distal cuff" 105.

Stent graft 10 generally includes a knitted graft liner 11, constructed for example, of Dacron®, that is integrated with stents 12 and 13 at either end. Stent graft 10 is generally threaded through a femoral artery using a delivery system that is per se known. Once stent graft 10 is positioned across aneurysm 101, as determined, for example, by radiography, stents 12 and 13 at the ends of the graft are deployed to anchor stent graft 10 to the nondilated portions of the aorta at proximal neck 104 and distal cuff 105.

As described briefly hereinabove, and in greater detail by T. Chuter et al. in *Endoluminal Vascular Prostheses*, Little Brown & Co. (1995), Chapter 2 at pp. 23–33, which is incorporated herein by reference, stent graft 10 is suitable for use only in those patients in which the nondilated portions of proximal neck 104 and distal cuff 105 are sufficiently long to permit stents 12 and 13 to be adequately deployed. In addition, variations in the aorta diameter above and below the aneurysm may exceed the capability of previously known stent grafts to properly engage the nondilated tissue at both the proximal and distal ends of the aneurysm.

Generally, if either of the above-described conditions occur more invasive surgical techniques must be employed to treat the aneurysm. If stent graft 10 were to be employed where either the proximal neck was too short (e.g. under 10 mm) or the distal cuff was too short or non-existent, proximal leakage path 106 and retrograde leakage path 107 would arise. Because flow paths 106 and 107 would continue to exert flow-induced pressure on the walls of aneurysm 101, risk of rupture of aneurysm 101 and the catastrophic consequences attending such a rupture would remain unabated by stent graft 10.

Figure 2:
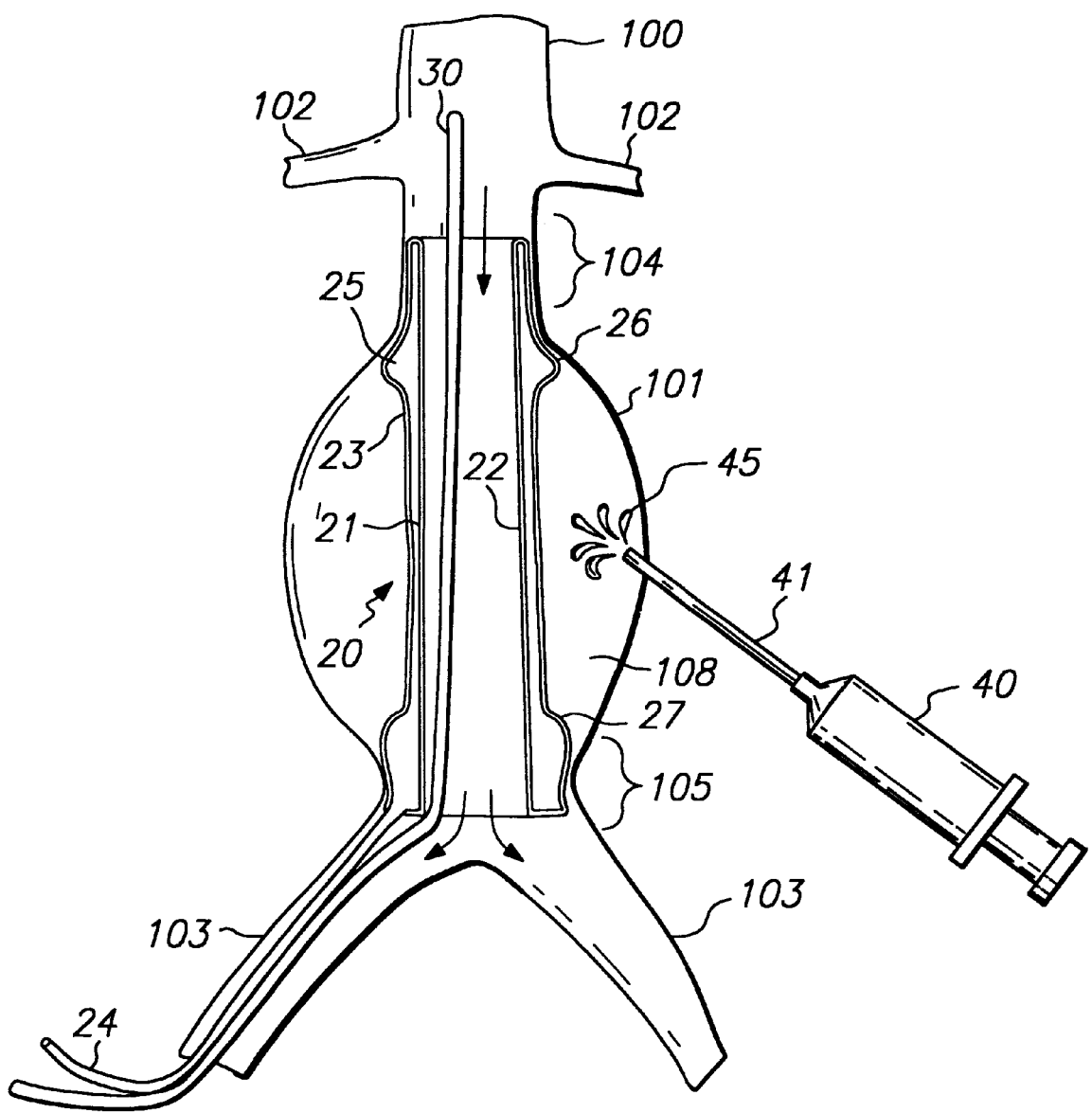
FIG. 2 is an elevation sectional view illustrating a first embodiment of the methods and apparatus of the present invention.

Referring now to FIG. 2, a first embodiment of the methods and apparatus of the present invention are described, in which like portions of aorta 100 are designated by like reference numerals. Apparatus constructed in accordance with the present invention is shown disposed across aneurysm 101 comprising hollow balloon catheter structure 20 disposed on guidewire 30.

Catheter structure 20 includes interior wall 21 forming central passageway 22, exterior wall 23, and lumen 24 for pressurizing cavity 25 formed by interior wall 21 and exterior wall 23. Catheter structure 20 may be formed of a suitably elastic material, such as polyester, polyethylene or polyvinyl chloride, and is delivered endoluminally to the site of the aneurysm in a collapsed state under fluoroscopic guidance, as is typical for balloon catheters. Catheter structure 20 may include bands of suitable material to provide fluoroscopic contrast to assist in guiding the catheter structure to a desired location.

As will of course be understood by one of skill in the art of angioplasty catheter design, catheter structure 20 alternatively may have a mechanical structure formed of a tight woven metallic or polymeric structure, and thus include a mechanically expansible, rather than balloon inflated, deployed mechanism.

When deployed in aorta 100, blood flows freely through central passage 22 of catheter structure 20 to iliac arteries 103, while blood-filled cavity 108 is created between the walls of the aneurysm and the exterior wall 23 of catheter structure 20.

Catheter structure 20 may have a uniform outer diameter when inflated via lumen 24, or may include additional volumes of expandable material at the proximal and distal ends to form cuffs 26 and 27 as shown in FIG. 2. Cuffs 26 and 27 may be used to improve the seal between catheter structure 20 and proximal neck 104 and distal cuff 105 of aneurysm 101, respectively, so as to minimize communication between blood passing through central passage 22 and the volume captured in cavity 108.

Catheter structure 20 may be constructed with exterior wall 23 of a compliant material so as to conform to the anatomy of the proximal neck and distal cuff, and a less compliant, but pliable material along interior wall 22, for example, by controlling the density of the material used to construct catheter structure 20 during the manufacturing process.

Figure 3:
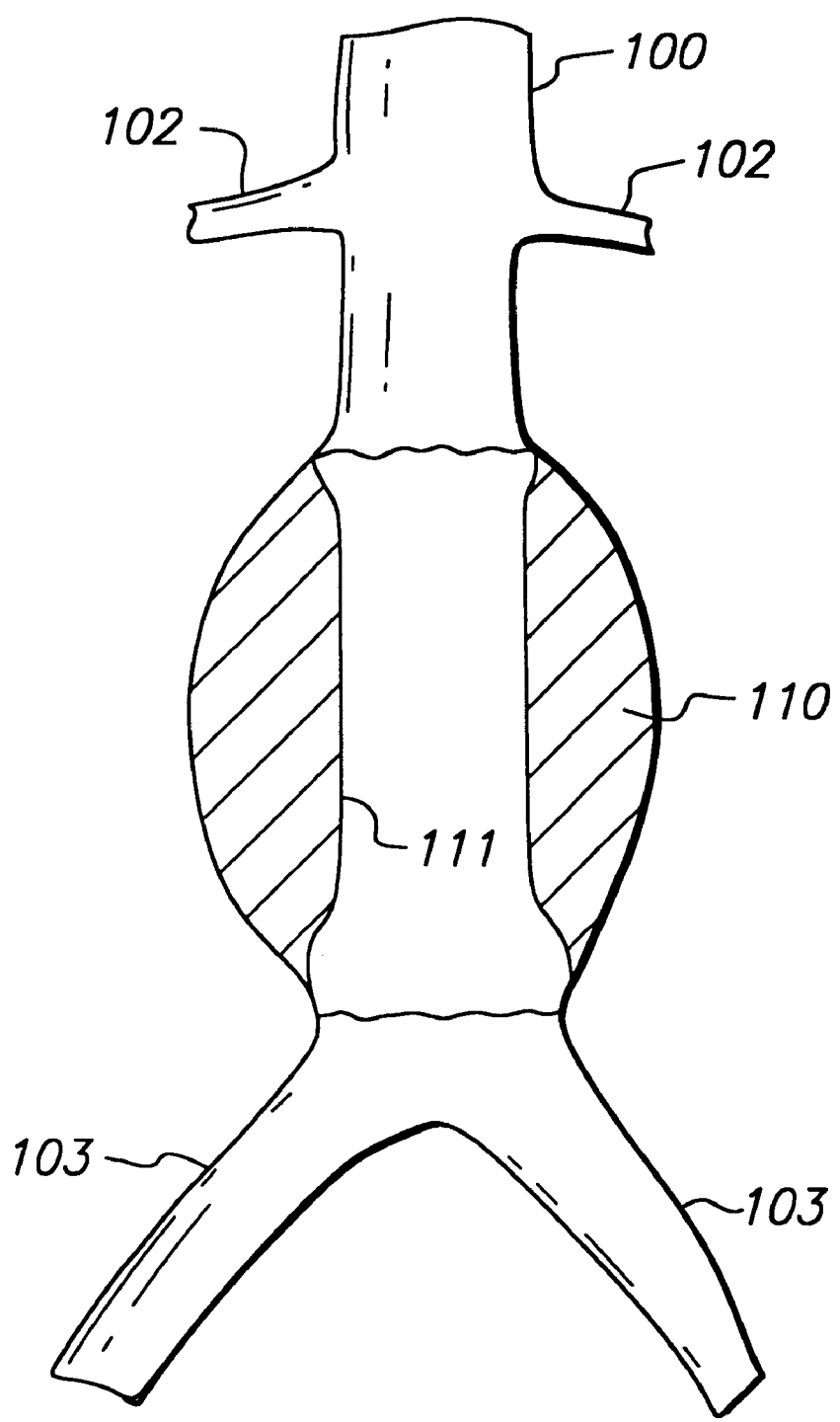
FIG. 3 is an elevational sectional view of a molded mass forming the relined inner surface of an aneurysm.

Still referring to FIG. 2, injection device 40 includes needle 41 that enters cavity 108 of aneurysm 101 either surgically or under laparoscopic guidance. If inserted laparoscopically, needle 41 may thus be introduced to the region of aneurysm 101 via a conventional trocar tube. In accordance with the present invention, injection device 40 delivers into cavity 108 substance 45, for example, a hardening agent or molding material (described below), that solidifies, or causes the blood captured in cavity 108 to solidify, into a coherent mass 110, as shown in FIG. 3.

Substance 45 may comprise a biological hardening agent, such as fibrin, that induces the blood captured in cavity 108 to form a coherent mass, or it may comprise a tissue material, such as collagen, which expands to fill the cavity. If fibrin is employed, it may be separated out of a sample of the patient's blood prior to the procedure to treat the aneurysm, and then injected into cavity 108 to cause thrombosis. On the other hand, collagen-based products, such as are available from Collatec, Inc., Plainsboro, N.J. may be used either to trigger thrombosis of the volume of blood in cavity 108, or for non-vascular organs or vessels, to fill cavity 108.

Alternatively, substance 45 may comprise a synthetic molding material, such as a starch-based poly ethylene glycol hydrogel or a polymer, such as polycapro-lactone, that is heat hardenable or hydrophilic. In a preferred embodiment of the invention, a starch-based poly ethylene glycol hydrogel is used that swells when exposed to an aqueous solution. Hydrogels suitable for use with the present invention may be obtained, for example, from Gel Med, Inc., Bedford, Mass. Hydrogels or polymers may also be selected to harden, for example, upon exposure to body temperature or blood pH. In addition, catheter structure 20 may further include a resistively heated winding disposed on its outer surface (not shown) to activate hardening of substance 45.

As yet a still further alternative, substance 45 may comprise a composite of helical polyester and platinum fiber coils, such as available from Target Therapeutics, Inc., Fremont, Calif. that induces thrombosis of the blood within cavity 108.

Referring still to FIG. 2, substance 45 is injected into cavity 108 between aneurysm 101 and exterior wall 23 of catheter structure 20 so as to induce the blood captured in cavity 108 to form a coherent thrombotic mass, or in the case of synthetic molding materials, to entirely fill the cavity and form a solid mass. It is expected that, depending upon the type of hardening agent or molding material used, solidification of the content of cavity 108 of aneurysm 101 may take about ten minutes or less. The balloon of catheter structure 20 is then deflated, and the hollow balloon catheter structure 20 and guidewire 30 are withdrawn.

As shown in FIG. 3, the solidified mass formed in cavity 108 resulting from the addition of the hardening agent or molding material creates mass 110 having passageway 111. Passageway 111 becomes incorporated in the blood flow path upon removal of catheter structure 20. To facilitate removal of catheter structure 20 from solidified mass 110, exterior wall 23 of catheter structure 20 may be coated with a suitable adherent (i.e., non-stick) coating, for example, Teflon®, a registered trademark of the E. I. duPont de Nemours Company, Wilmington, Del. (polytetrafluorethylene), or other suitable biocompatible material, such as Parylene®, available from Paratech, Inc., Aliso Viejo, Calif.

Figure 4:
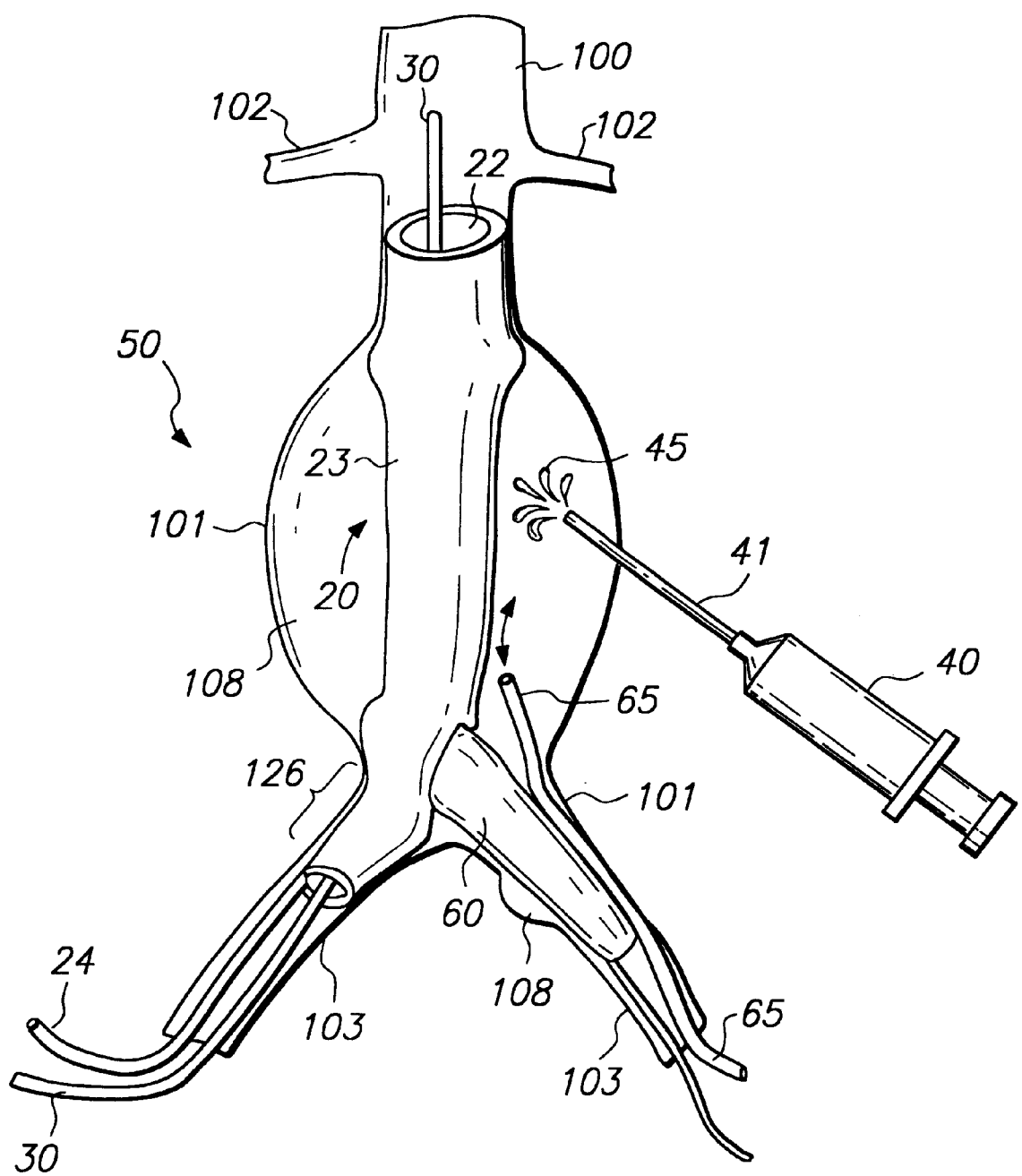
FIG. 4 is an elevation view, partly in section, of an alternative embodiment of the apparatus of the present invention for excluding an aneurysm that extends into the right branch of the iliac artery.

Referring now to FIG. 4, an alternative embodiment of the methods and apparatus of the present invention is described for use in situations where one or both external iliac arteries include aneurysms. In the embodiment of FIG. 4, like parts of the apparatus are again referenced with like numbers. Thus, apparatus 50 of the embodiment of FIG. 4 includes hollow balloon catheter structure 20, guidewire 30 and conventional balloon catheter 60 disposed in the right branch of the iliac artery and urged in abutment against the lower portion of catheter structure 20.

Catheter structure 20 includes an elastic outer membrane forming exterior wall 23 and includes an inner wall 21 forming passageway 22. Catheter structure 20 is mounted for deployment along guidewire 30 from a collapsed state in which it is delivered to the site of the aneurysm via a femoral artery. Unlike the hollow balloon catheter structure of FIG. 2, catheter structure 20 of FIG. 4 includes tapered lower portion 126 that extends into the left iliac artery.

Balloon catheter 60 may be of conventional balloon catheter construction and is delivered endoluminally in a collapsed state into the right iliac artery via the corresponding femoral artery. In accordance with the present invention, balloon catheter 60 is delivered under fluoroscopic guidance to a location at which its distal end abuts against catheter structure 20. So long as completion of the treatment (i.e., injection and hardening of the cavity volume) is completed within about ten minutes or less, temporary blockage of blood flow in the iliac artery containing the conventional balloon catheter is not expected to cause any adverse effects.

Injection device 40 may then be positioned laparoscopically to inject substance 45 into cavity 108 defined by the walls of aneurysm 101 and the exterior walls of catheter structure 20 and balloon catheter 60. Substance 45, which again may be a hardening agent or molding material as described hereinabove, is then injected into cavity 108 to solidify the blood captured in cavity 108 into a coherent mass. Catheter structure 20 and balloon catheter 60 are then deflated and withdrawn, restoring blood flow to the iliac bifurcation via the new passages created in the solidified mass 110, similar to mass 110 of FIG. 3.

Alternatively, or in addition to injection device 40, catheter 65, which may be a multi-lumen catheter, may be employed as shown in FIG. 4. Catheter 65 is positioned with its distal end located in cavity 108 prior to inflation of balloon catheter 60, and may be used to inject substance 45 into cavity 108 instead of injection device 40 and needle 41. Catheter 65 may also be used to aspirate part of the volume of cavity 108, and to replace a controlled amount of the aspirated material with an appropriate hardening agent or molding material, thereby reducing the size of the aneurysm from its untreated condition.

If catheter 65 is used in the above-described manner to aspirate cavity 108 of aneurysm 101 prior to solidification of the contents of cavity 108, the excess tissue of the shrunken aneurysm may then be laparoscopically or surgically stapled, thus permanently reducing the size of the aneurysm and relieving pressure from the aneurysm on adjacent organs.

As will of course be apparent to one of skill in the art from the foregoing description, catheter 65 may be used with equal ease and to produce similar results with the embodiment of FIG. 2, either alternatively or in addition to injection device 40.

Figure 5:
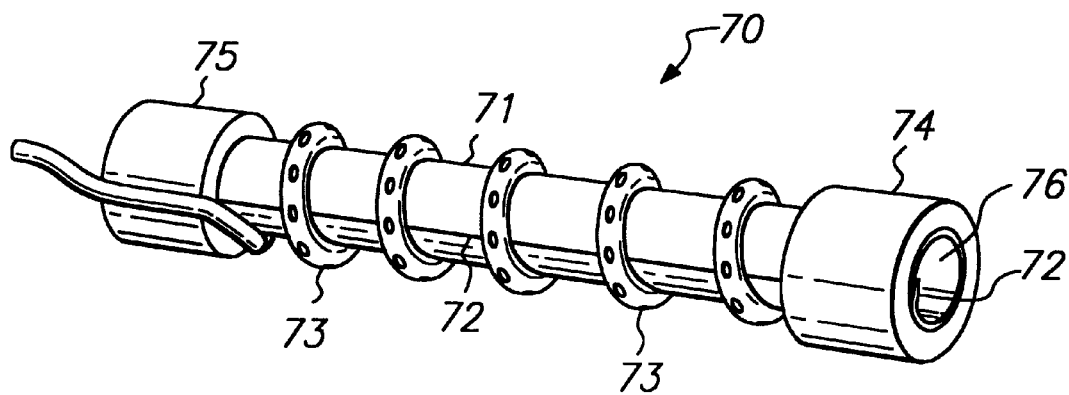
FIG. 5 is a perspective view of the aneurysm exclusion/injection portion of an alternative embodiment of an apparatus constructed in accordance with the present invention.
Figure 6:
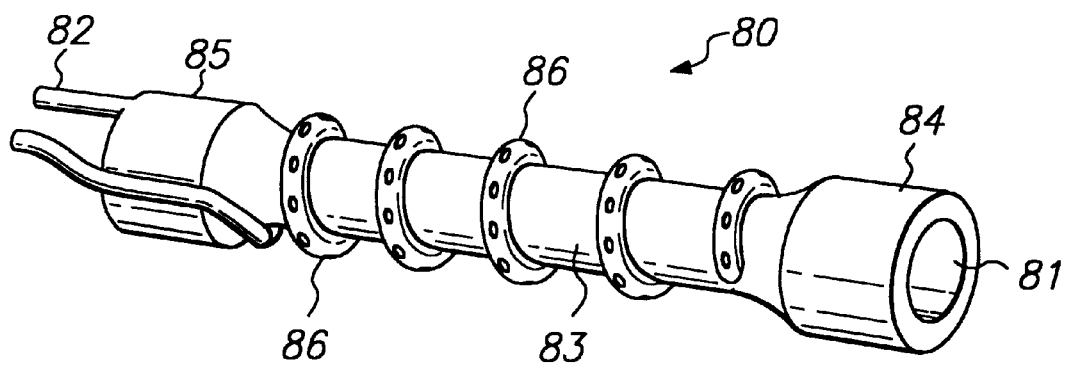
FIG. 6 is a perspective view of an alternative embodiment of the apparatus of FIG. 5.

With respect to FIGS. 5 and 6, the distal ends of two further alternative embodiments of the apparatus of the present invention are described. Only the balloon catheter elements of the apparatus are illustrated in FIGS. 5 and 6, since the proximal ends of the catheters, including the stop-cock and guidewire arrangements, are well-known to those of skill in the art of balloon angioplasty and catheter design.

Referring to FIG. 5, an alternative configuration to hollow balloon catheter structure 20 of FIG. 2 is described. Balloon apparatus 70 includes rolled sheet 71 having overlapping edges 72, and spiral porous balloon 73 wrapped along the length of rolled sheet 71. Cuff mechanisms 74 and 75, which may be inflatable, are disposed at the proximal and distal ends of balloon apparatus 70, and may be inflated by a non-porous lumen of spiral balloon 73 specifically connected to cuffs 74 and 75.

As described below, balloon apparatus performs the functions of not only catheter structure 20 of FIG. 2 (by providing a mold for solidification of the aneurysm cavity), but also provides the functions of injection device 40 (or catheter 65), as described hereinabove. Rolled sheet 71 may comprise a polyurethane material, while cuff mechanisms 74 and 75 may comprise a suitable elastic material, for example, poly vinyl chloride. Alternatively, cuff mechanisms 74 and 75 may employ a suitable mechanically expansible (non-inflatable) arrangement, and appropriate means for actuating such an arrangement.

In operation, balloon apparatus 70 is endoluminally delivered to the site of the aneurysm under fluoroscopic guidance in a collapsed state. In its collapsed state, rolled sheet 71 is wound snugly against the delivery catheter, and spiral porous balloon 73 and cuff mechanisms 74 and 75 are likewise collapsed against the rolled sheet 71. Once located in position within the aneurysm, so that cuff mechanisms 74 and 75 are disposed adjacent to the proximal neck and distal cuff (or iliac bifurcation), respectively, cuffs 74 and 75 are actuated to exclude the aneurysm from communication with central passage 76 within rolled sheet 71.

As will of course be understood, actuation of cuff mechanisms 74 and 75 will cause rolled sheet 71 to unroll slightly and attain a larger internal diameter, while overlapping edges 72 prevent blood captured in the cavity (defined by the exterior of balloon apparatus 70 and the walls of the excluded aneurysm) from communicating with blood flowing through central passage 76.

Once apparatus 70 is disposed across the aneurysm and cuff mechanisms 74 and 75 deployed, the hardening agent or molding material, as described hereinabove, is injected into the cavity between the aneurysm and the outer surface of rolled sheet 71 via spiral porous balloon 73. When the mass of blood or molding material has solidified into a coherent mass, cuffs 74 and 75, and porous spiral balloon 73 are deflated and withdrawn. To facilitate deflation and withdrawal of apparatus 70 from the solidified mass formed in the aneurysm, the outer surfaces of apparatus 70 may be coated with Teflon® or other suitable biologically compatible non-stick material.

Referring now to FIG. 6, a further alternative embodiment of balloon apparatus 70 of FIG. 5 is described. Balloon apparatus 80 comprises a hollow balloon catheter structure as described with respect to FIG. 2 on which a spiral porous balloon is mounted, as for the embodiment of FIG. 5. In particular, balloon apparatus 80 includes interior passage 81, pressurizing lumen 82 and inflatable exterior surface 83 (which may have a uniform outer diameter or include proximal and distal cuffs 84 and 85), and spiral porous balloon 86 through which the hardening agent or molding material is injected into the excluded aneurysm.

Operation of balloon apparatus of FIG. 6 is similar to that described above with respect to the embodiment of FIG. 5. Specifically, balloon apparatus 80 is first delivered endoluminally to the site of the aneurysm under fluoroscopic guidance in a collapsed state. Balloon apparatus 80 is then pressurized via lumen 82 to exclude the aneurysm from the blood flow path while permitting continued flow through passage 81. A suitable hardening agent or molding material is then introduced into the cavity in the aneurysm via porous spiral balloon. Once the mass in the aneurysm is solidified, balloon apparatus 80 is then deflated and withdrawn, again leaving a "relined" aneurysm passage similar to that shown in FIG. 3.

Figure 7:
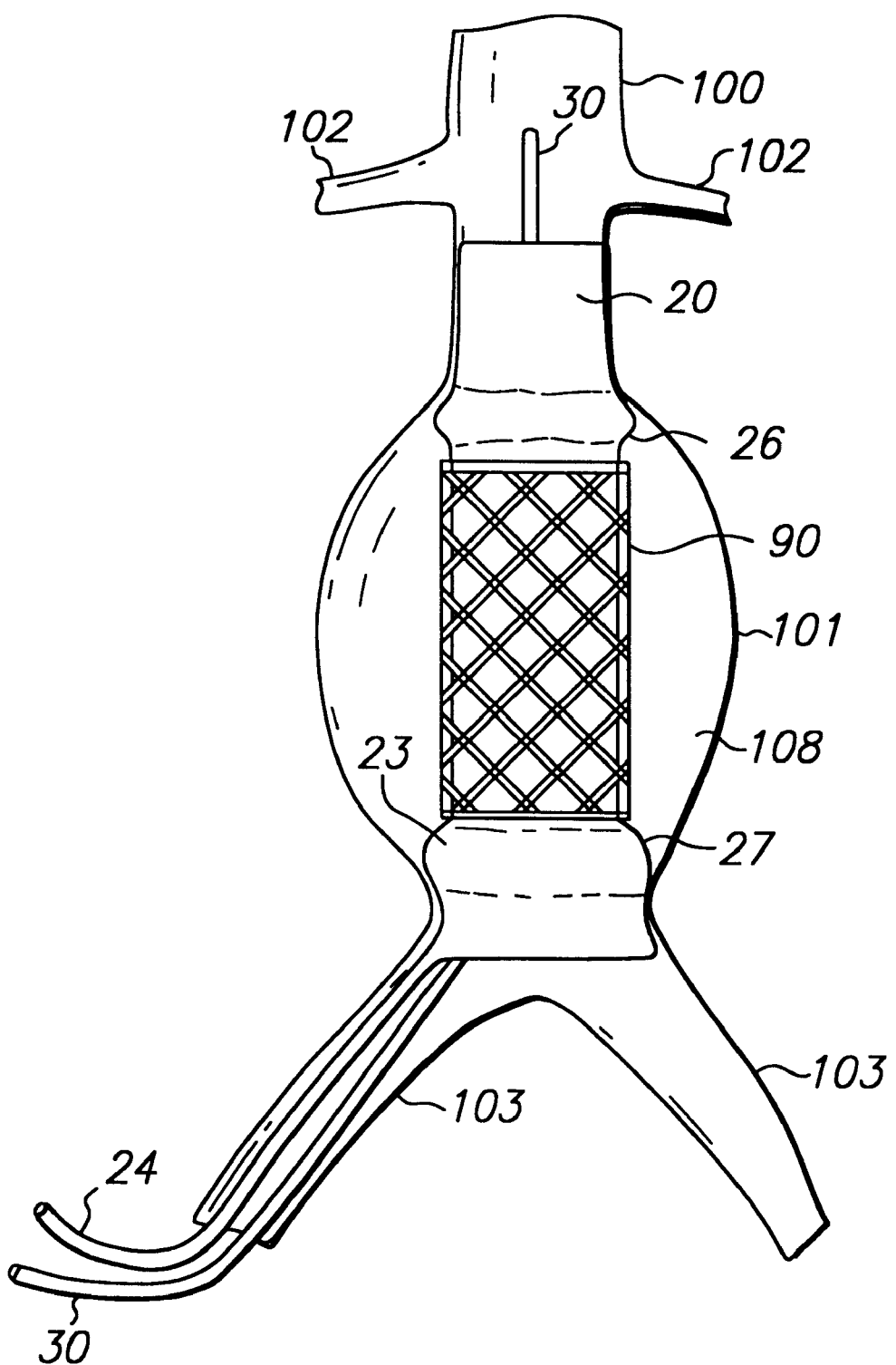
FIG. 7 is an elevational view of a mesh member disposed on the apparatus of FIG. 2.
Figure 8:
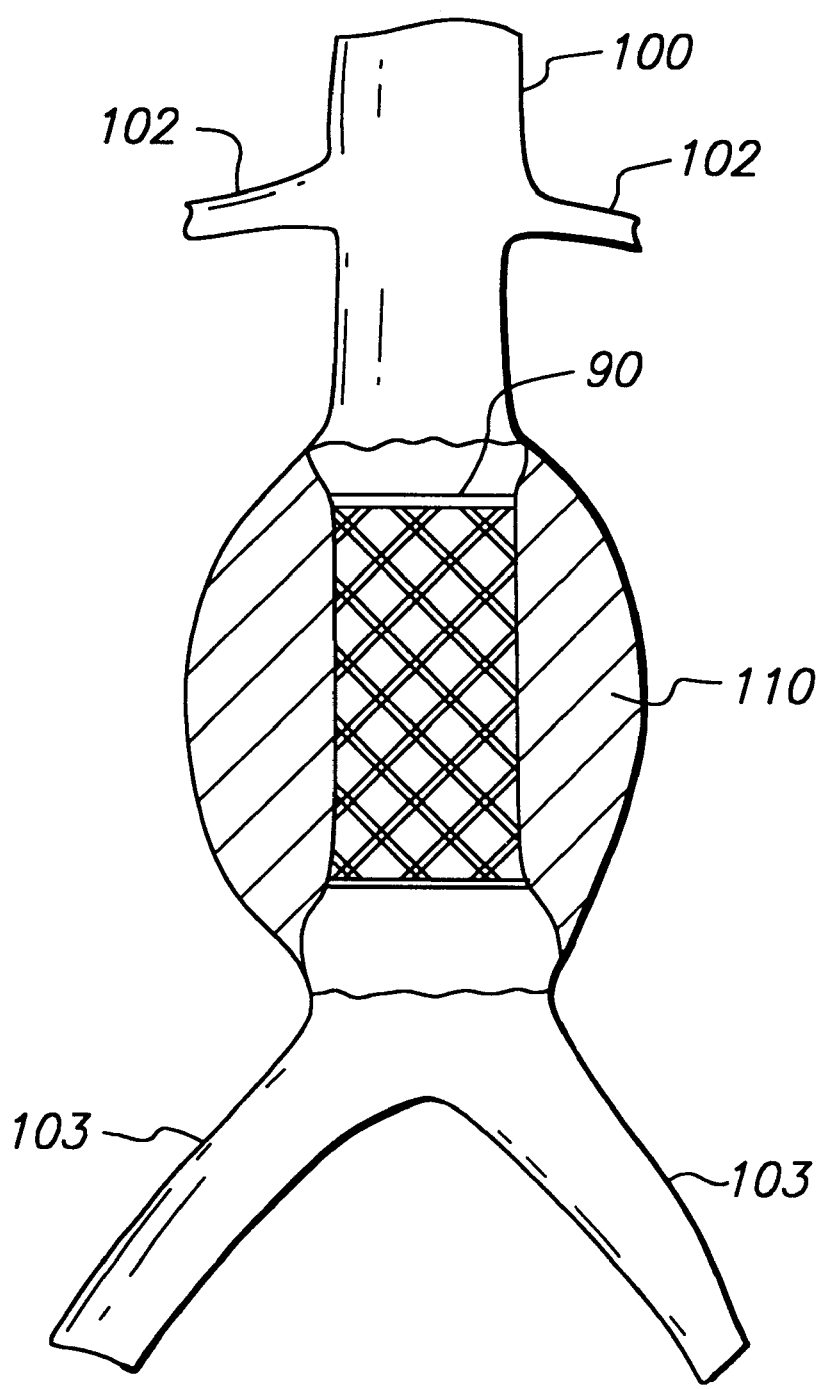
FIG. 8 is a sectional view similar to that of FIG. 3, showing the mesh member of FIG. 7 integrated with the molded mass formed within the aneurysm.

With respect to FIGS. 7 and 8, an exemplary configuration of mesh 90 for use with the catheter structure of FIG. 2 is described. Mesh 90 comprises a thin wire or polymeric net or mesh disposed around the exterior wall 23 of hollow balloon catheter structure 20. Mesh 90 is placed around catheter structure 20 prior to delivery of catheter structure 20 endoluminally to the aneurysm site, and may be self-expanding or expanded by inflation of catheter structure 20.

When the molding material or hardening agent is introduced into cavity 108 of aneurysm 101, mesh 90 becomes incorporated into the solidifying mass 110 (see FIG. 8), and is expected to reduce embolization of the molding material or hardening agent, and thus reduce the risk of thrombosis downstream from mass 110. Upon completion of the hardening of the volume of cavity 108, hollow balloon catheter structure 20 is deflated, and mesh 90 is left in position within the aneurysm, where it forms part of the relined passage of the aorta.

It will of course be understood by those skilled in the relevant arts that the exemplary embodiments of the invention described hereinabove in no way limit the intended use of the methods and apparatus of the present invention, and that the methods of the present invention could be implemented using catheter structures having other configurations.

In addition, while the methods and apparatus of the present invention have been described with reference to excluding aneurysms occurring in the abdominal aorta, the methods and apparatus of the present invention are equally applicable to gastro-intestinal, respiratory, reproductive organ, urethral applications and elsewhere where it is desirable to "reline" a hollow-body organ or vessel.

Thus, for example, the methods and apparatus of the present invention may be used to treat arterio-venous fistulas in a manner similar to that described above for the aorta. Application of the present invention in such treatment is consistent with the use of previously-known stent-graft techniques in treatment of such fistulas, as described, for example, in the above-mentioned T. Chuter et al. text, *Endoluminal Vascular Prostheses*, at Chapter 10 at pp. 217–235, which is incorporated herein by reference. The methods and apparatus of the present invention are expected to provide even greater flexibility in the treatment of such abnormalities.

While preferred illustrative embodiments of the present invention are described above, it will be obvious to one skilled in the art that various changes and modifications may be made therein without departing from the invention and it is intended in the appended claims to cover all such changes and modifications which fall within the true spirit and scope of the invention.

What is claimed is:

1. A method of treating an aneurysm or arterio-venous fistula in a body vessel or hollow organ comprising proximal and distal necks on either side of an enlarged cavity, the method comprising:

providing a tubular member having first and second ends and a passageway extending therebetween, the tubular member being expandable between a contracted state to facilitate endoluminal delivery, and a deployed state larger than the contracted state, the passageway being substantially open in the deployed state;

delivering the tubular member in the contracted state to a position extending across the aneurysm or arterio-venous fistula;

expanding the tubular member into the deployed state such that the first and second ends sealingly engage the proximal and distal necks, and the passageway is substantially opened, thereby excluding the cavity from communicating with the passageway while allowing flow to continue through the body vessel or hollow organ via the passageway;

injecting a solidification substance into the cavity; and withdrawing the tubular member from the body vessel or hollow organ to create a flow path at least partially defined by the solidification substance that extends through the cavity.

2. The method of claim 1, further comprising the step of collapsing the tubular member from the deployed state to facilitate withdrawal.

3. The method of claim 1, wherein the tubular member includes a first annular-shaped expandable member on or near the first end, the first annular-shaped expandable member being collapsed in the contracted state and expanded in the deployed state.

4. The method of claim 3, wherein the tubular member includes a second annular-shaped expandable member on or near the second end, the second annular-shaped expandable member being collapsed in the contracted state and expanded in the deployed state.

5. The method of claim 1, wherein the step of injecting a solidification substance comprises injecting a synthetic molding agent, a biological hardening agent, or a filler material into the cavity.

6. The method of claim 1, wherein the tubular member includes a lumen communicating with an exterior surface of the tubular member, and wherein the step of injecting a solidification substance into the cavity comprises injecting the solidification substance through the lumen into the cavity.

7. The method of claim 6, wherein the lumen comprises an inflatable balloon attached to the tubular member, the method further comprising the step of inflating the balloon before the solidification substance is injected into the cavity.

8. The method of claim 1, further comprising:

providing an injection device having a needle; and inserting the injection device under laparoscopic guidance so that the needle enters the cavity;

wherein the solidification substance is injected into the cavity from the injection device.

9. The method of claim 1, further comprising the step of providing an expandable stent disposed on the tubular member, the stent having a contracted delivery state and an expanded deployed state, wherein the step of delivering the tubular member includes delivering the stent in its contracted state across the aneurysm or arterio-venous fistula.

10. The method of claim 1, wherein the body vessel or hollow organ is an aorta, and the aneurysm or arterio-venous fistula includes a portion of the aorta and at least one of first and second iliac arteries.

11. The method of claim 10, wherein the step of delivering the tubular member includes positioning the tubular member so that the second end extends into the aorta and the first end extends into the first iliac artery, the method further comprising:

delivering an inflatable balloon into the second iliac artery so that a distal end of the balloon is urged against a portion of the tubular member; and inflating the balloon such that the cavity is substantially sealed from the second iliac artery.

12. The method of claim 11, further comprising the step of deflating and withdrawing the balloon, the flow path comprising first and second iliac flow paths extending from the aorta into the first and second iliac arteries.

13. An apparatus for treating an aneurysm or arterio-venous fistula in a body vessel or hollow organ, the apparatus comprising a tubular member having first and second ends and a passageway extending therebetween, the tubular member being expandable between a contracted state to facilitate endoluminal delivery of the tubular member and a deployed state larger than the contracted state wherein the first and second end are expanded for engaging necks on either side of an aneurysm or arterio-venous fistula, the tubular member including an interior surface at least partially defining the passageway, and an exterior surface defining a cavity between the interior and exterior surfaces.

14. The apparatus of claim 13, further comprising a lumen in communication with the cavity connectable to a source of inflation media.

15. The apparatus of claim 13, further comprising an injection device operatively disposed with the tubular member for injecting a solidification substance adjacent to an outer surface of the tubular member.

16. The apparatus of claim 15, wherein the injection device is a porous member extending along the tubular member.

17. The apparatus of claim 16, wherein the porous member is a balloon having an inflation lumen and a solidification substance lumen in communication with pores in a wall of the balloon.

18. The apparatus of claim 15, wherein the porous member extends hectically around the tubular member.

19. The apparatus of claim 13, further comprising an inflatable cuff disposed on or near the first end.

20. The apparatus of claim 19, wherein the inflatable cuff comprises an enlarged region of the exterior surface of the tubular member.

21. The apparatus of claim 19, further comprising an inflatable cuff disposed on or near the second end.

22. The apparatus of claim 21, further comprising an inflatable balloon abut table against the tubular member for treating an aneurysm or arterio-venous fistula at or near a bifurcation.

23. The apparatus of claim 13, further comprising a stent disposed around the exterior surface, the stent having a contracted delivery state and an expanded deployment state.

24. An apparatus for treating an aneurysm or arterio-venous fistula in a body vessel or hollow organ, the apparatus comprising:
  a tubular member having first and second ends an a passageway extending therebetween, the tubular member being expandable between a contract d state to facilitate endoluminal delivery and a deployed state larger than the contracted state;
  an annular-shaped expandable member disposed on or near each of the first and second ends; and
  an injection device operatively disposed with the tubular member for injecting a solidification substance adjacent to an outer surface of the tubular member.

25. The apparatus of claim 24, wherein the injection device is a porous member extending along the tubular member.

26. The apparatus of claim 25, wherein the porous member is a balloon having an inflation lumen and a solidification substance lumen in communication with pores in a wall of the balloon.

27. The apparatus of claim 25, wherein the porous member extends hectically around the tubular member.

* * * * *

UNITED STATES PATENT AND TRADEMARK OFFICE
CERTIFICATE OF CORRECTION

PATENT NO.    : 6,231,562 B1
DATED         : May 15, 2001
INVENTOR(S)   : Khosravi et al.

Page 1 of 1

It is certified that error appears in the above-identified patent and that said Letters Patent is hereby corrected as shown below:

Column 2,
Lines 10 and 11, change "PCT/U.S. Ser. No. 94/09837" to -- PCT/US94/09837 --.

Column 6,
Line 9, change "polycapro-lactone" to -- poly-capro-lactone --.

Column 12,
Line 2, change "abut table" to -- abuttable --.

Signed and Sealed this

Seventh Day of May, 2002

Attest:

Attesting Officer

JAMES E. ROGAN
Director of the United States Patent and Trademark Office